United States Patent [19]
Haas

[11] Patent Number: 5,952,580
[45] Date of Patent: Sep. 14, 1999

[54] APPARATUS AND METHOD FOR PRODUCING SHAFTS HAVING PRESELECTED LENGTHS AND FLEXURAL PROPERTIES

[75] Inventor: Neal Haas, San Diego, Calif.

[73] Assignee: Grafalloy, El Cajon, Calif.

[21] Appl. No.: 08/941,477

[22] Filed: Sep. 30, 1997

[51] Int. Cl.[6] .............................. G01N 19/06; G01N 3/00
[52] U.S. Cl. ................................. 73/783; 73/794; 73/853
[58] Field of Search ..................... 73/65.03, 853, 73/814, 650, 849, 579, 854, 794, 65.07, 783; 144/359, 2.1

[56] References Cited

U.S. PATENT DOCUMENTS

| | | |
|---|---|---|
| 4,122,593 | 10/1978 | Braly .......................................... 29/407 |
| 4,455,022 | 6/1984 | Wright .................................... 273/77 A |
| 4,682,504 | 7/1987 | Kobayashi ................................. 73/854 |
| 4,869,304 | 9/1989 | Gore ......................................... 144/354 |
| 5,379,641 | 1/1995 | Paasivaara et al. ........................ 73/579 |
| 5,478,073 | 12/1995 | Hackman ............................... 273/77 A |

*Primary Examiner*—Hezron Williams
*Assistant Examiner*—Helen C. Kwok
*Attorney, Agent, or Firm*—Gregory Garmong

[57] ABSTRACT

A golf club shaft blank is clamped at its butt end and deformed at its tip end to establish the longitudinal deformation characteristics of the shaft blank. The shaft is repositioned relative to the clamp and then reclamped at a new location which, when deformed, has the desired longitudinal deformation characteristics. The shaft is sawed to the desired length by removing material from the butt end and the tip end of the shaft.

15 Claims, 2 Drawing Sheets

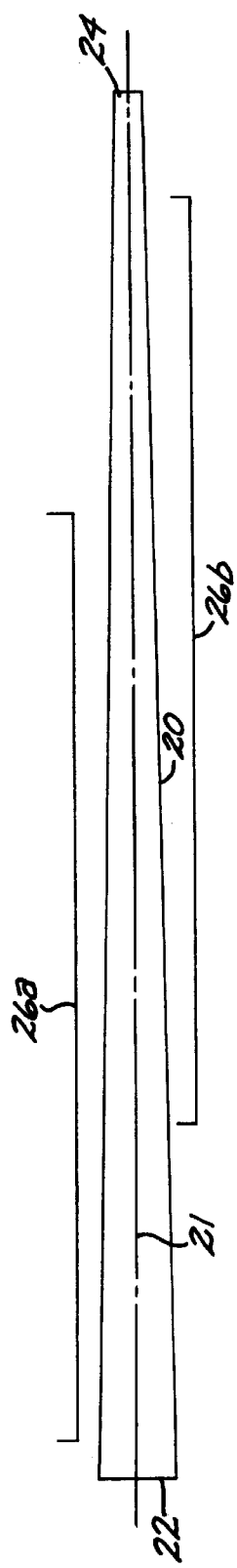
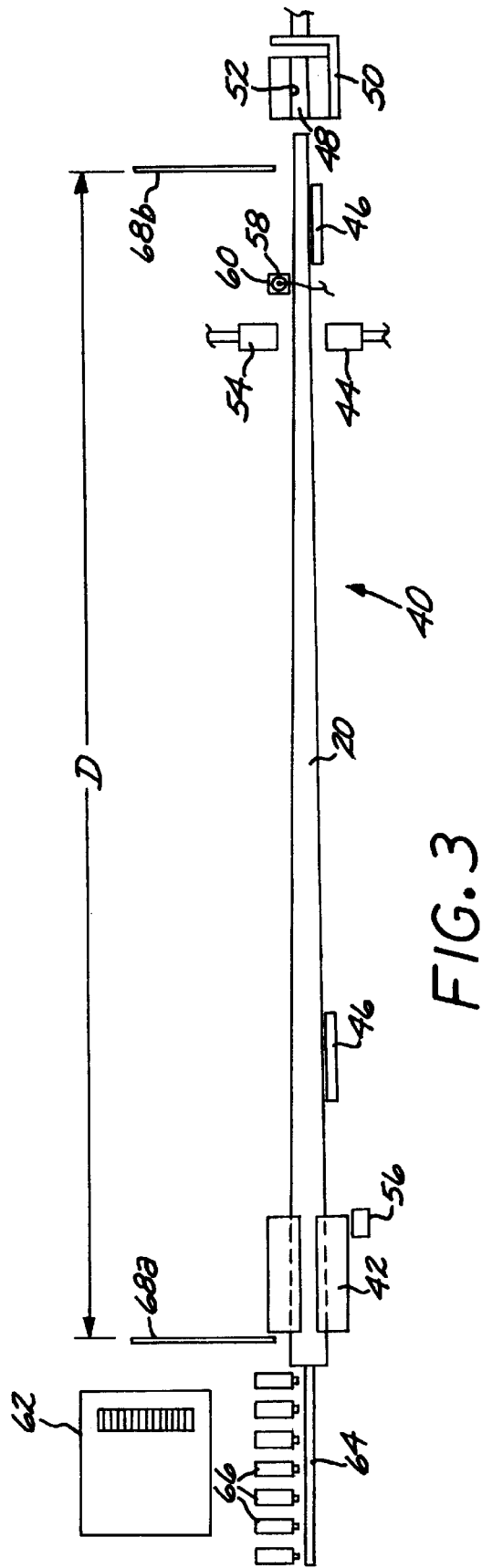
FIG. 1
FIG. 3

APPARATUS AND METHOD FOR PRODUCING SHAFTS HAVING PRESELECTED LENGTHS AND FLEXURAL PROPERTIES

BACKGROUND OF THE INVENTION

This invention relates to the production of golf club shafts, and, more particularly, to an approach for trimming golf club shaft blanks to as to have a desired final length and final deformation characteristics.

A golf club includes a thin, elongated shaft and a head affixed to one end of the shaft. Golf club shafts are typically made of a metal such as steel or titanium, or a composite material. In use, the club is swung by the standing golfer through an arc so that the head impacts a golf ball at ground level.

The shaft must be of the correct length for comfortable use by the golfer, and clubs are therefore manufactured and sold according to shaft length. Additionally, it is known that the hitting characteristics of the golf club are determined in part by the longitudinal deformation properties of the club shaft. The flexibility of the shaft (within limits), significantly affects the velocity of the club head as it impacts the ball and the expected fight distance of the ball. However the more flexible shafts are more difficult to control during the swing and require a greater skill level of the golfer. Consequently, golf club shafts may be made in a range of flexibilities for each length, with the selection of flexibility made by the golfer according to skill level and the intended use of the club.

Shafts made of a composite material such as carbon fibers embedded in an epoxy matrix are prepared by collating plies of an uncured prepreg composite material onto a form or in mold, and subsequently consolidating and curing the layup. The shafts are generally of a desired configuration with approximately the designed properties. However, due to variations in the starting material and in the fabrication procedure, there is typically a variation in the longitudinal flexural properties in a group of shafts of up to about ±5 percent from the nominal value. This variation, while acceptable for some circumstances, is too large for premium-quality clubs, where the variation should be no more than about ±1–2 percent from the nominal value.

A number of processing modifications may be made to the production operation. In order to reduce the property variation of the final acceptable shafts from the nominal. For example, the starting material may be more stringently screened and selected, greater care may be taken in the fabrication processing, the finished shafts may be individually hand processed to adjust their properties, or the unusable shafts may be diverted or scrapped. All of these alternatives significantly increase the cost of the acceptable shafts that meet the property-variation limitation indicated above, which may be acceptable for custom shafts but are not acceptable for shafts intended for mass markets.

There is a need for an approach to fabricating golf club shafts which are of the correct length and also have longitudinal flexure properties very close to a nominal value. The present invention fulfills this need, and further provides related advantages.

SUMMARY OF THE INVENTION

The present invention provides an apparatus and a method for producing golf club shafts having lengths and longitudinal flexural properties within small variations of nominal designed values. The apparatus automatically and without operator intervention determines the flexural properties of a shaft, positions the shaft to be cut to length such that the resulting trimmed shaft has the desired flexural properties, and trims the shaft to the exact length and required flexural properties. The apparatus allows the operator to select the nominal values of the length and flexural properties, as well as the acceptable limits of the flexural properties.

In accordance with the invention, an apparatus is provided for trimming a golf club shaft elongated parallel to a longitudinal direction and having a butt end and a tip end. The apparatus comprises an actuatable butt clamp sized to clamp the shaft at a location adjacent to its butt end, means for measuring the longitudinal deformation (e.g., frequency or deflection) of the shaft with the butt clamp engaged to the shaft at a first location along the length of the shaft, means for longitudinally repositioning the shaft responsive to the means for measuring and for reclamping the shaft using the butt clamp at a second location along the length of the shaft, and a pair of saws spaced a selected distance apart and operable to saw the shaft at a first saw location adjacent to the butt end and at a second location adjacent to the tip end, with the shaft clamped at the second location.

To use the apparatus, a shaft blank is made overly long, typically about 2 inches longer than the final shaft is to be. The shaft is mounted into the machine and clamped near its butt end. The longitudinal flexural characteristics are measured by any operable approach, such as flexural vibration or dead-weight loading. The clamping force is released, and the shaft is repositioned by moving it longitudinally in the clamp to a location at which the resulting shaft will have the required longitudinal flexural properties. The clamping force is reapplied at a second location, and the shaft blank is trimmed to length by the two saws spaced apart by exactly the required shaft length. The shaft is ejected from the machine, and the process is repeated for another shaft.

This approach depends upon the recognition of the characteristics of the shaft. The shaft blank is slightly tapered from its butt end to its tip end. The longitudinal flexure characteristics of each shaft blank are first determined from an arbitrarily clamping location near the butt end. By changing the longitudinal location of the shaft blank relative to the saws and then clamping the shaft blank at the new location, either more or less of the heavier material near the butt end (or equivalently, less or more of the lighter material near the tip end) may be included in the final shaft after the saw trimming. This approach is feasible because the longitudinal flexure properties of the as-fabricated shaft blanks are reasonably close to the nominal value. If they were too greatly different from the nominal value, the fine tuning approach of the present invention would not be possible.

Studies with a prototype of the present apparatus have shown that composite-material wood and iron shafts with exact lengths and flexure properties within about ±1–2 percent of the nominal value may be fabricated. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIG. 1 is a schematic illustration of a golf shaft blank;

FIG. 3 is a schematic illustration of a preferred machine according to the invention.

DETAILED DESCRIPTION OF THE INVENTION

Figure 2:
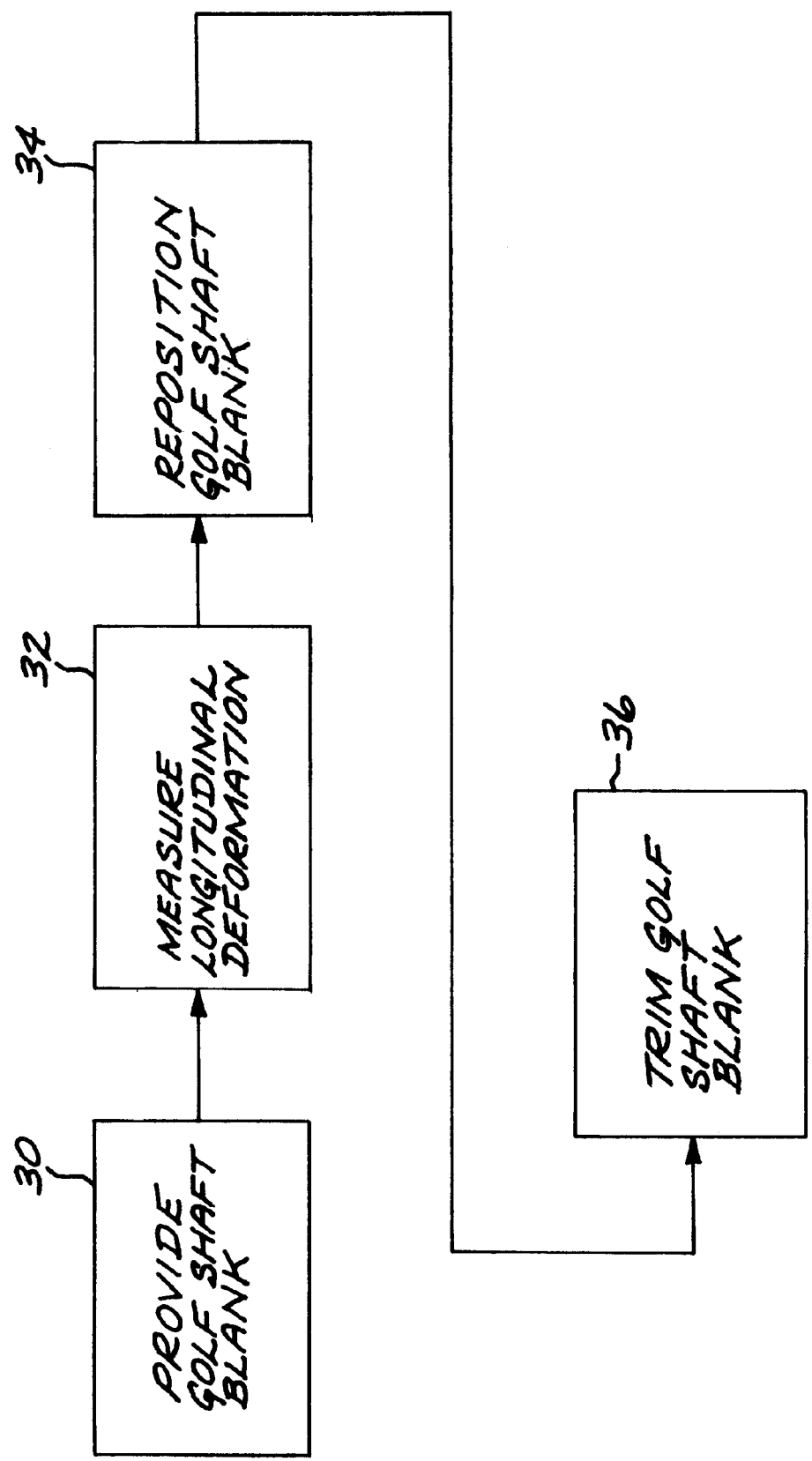
FIG. 2 is a block flow diagram of the preferred approach of the invention.

FIG. 1 illustrates a golf shaft blank 20. The golf shaft blank 20 is in the form of a hollow tapered cylinder having a longitudinal axis 21. The golf shaft blank 20 is tapered at an angle of about 1 degree from a blank butt end 22 to a blank tip end 24. The taper is exaggerated in FIG. 1 for illustration.

FIG. 1 also illustrates the principle of the attaining of specific flexural properties by selective trimming of the length of the golf shaft blank 20. The golf shaft blank 20 is made longer than necessary for the nominal desired length of the final shaft. If the final shaft is to be made a preselected length and be very stiff, material is trimmed primarily from the blank tip end 24, with the final shaft extending over the trimmed length 26a. If the final shaft is to be of the same length but more flexible, material is trimmed primarily from the blank butt end 22, with the final shaft extending over the trimmed length 26b. Once again, the positioning of these lengths is exaggerated for illustration.

A preferred method of practicing the invention is illustrated in FIG. 2. The tapered golf shaft blank 20 is provided, numeral 30. The golf shaft blank 20 is made longer than required for the nominal desired length. For example, if the final club is to be about 39 inches long, the shaft blank is preferably made about 41 inches long. The shaft blank 20 is preferably made of a composite material of carbon fibers embedded in an organic matrix material such as an epoxy. The golf shaft blank 20 is fabricated by any operable technique, but the well known procedures of flag rolling and bladder molding are the two preferred approaches. With these conventional fabrication techniques, the shaft blank 20 is typically made to within about ±5 percent of the desired nominal deformation value in an economical manner. If a closer tolerance is desired in the as-prepared shaft blank, the cost of preparation increases due to the need to be more selective in the material of construction and to take more care in collation, consolidation, and sanding procedures. The present approach provides for automatically measuring and trimming the overly long shaft blank 20 to the desired length and so as to achieve the closer tolerances to the nominal longitudinal flexural value.

The remaining steps are performed with the shaft blank 20 mounted in a single measurement and trimming apparatus 40, illustrated in FIG. 3. The shaft blank 20 is mounted in the apparatus 40 by grasping the butt end 22 in an actuatable butt clamp 42 while holding the tip end steady and in the proper orientation using a tip support 44. The mounting of the shaft blank 20 may be accomplished by hand or, more preferably, using an automated loading apparatus such as a pair of loading arms 46 that position the shaft blank 20 in the butt clamp 42 and on the tip support 44.

The longitudinal deformation of the shaft blank 20 is measured, numeral 32. A weight is installed on the blank tip end 24. The weight may be of any operable form, such as a suspended weight or, more preferably as shown, a collet 48 that fits around the tip end. The collet 48 is installed by a collet service rod 50 which moves the collet 48 laterally (from right to left in the illustration) so that the blank tip end 24 fits within a bore 52 in the center of the collet 48. After the collet 48 is installed, the collet service rod 50 is withdrawn, to the right in the view of FIG. 3. The tip support 44 is retracted downwardly so that the blank tip end 24 is no longer supported, creating a cantilevered configuration with the blank tip end 24 supported solely from its blank butt end 22 by the butt clamp 42.

The blank tip end 24 is forced downwardly by a shaft exciter rod 54 that pushes it downwardly. Once the blank tip end 24 has been forced downwardly to the desired extent, typically about 3–4 inches, the collet service rod 50 is translated to a position (to the left in the view of FIG. 3) where it holds the blank tip end 24 in its full downwardly deformed position.

The golf shaft blank 20 is caused to oscillate by withdrawing the collet service rod 50 (to the right in the view of FIG. 3), thereby releasing the golf shaft blank 20 from its downwardly stressed position and allowing it to oscillate upwardly and downwardly. The time required to complete a preselected number of oscillations is measured. The number of oscillations is measured in any operable manner. In the preferred approach, the butt clamp 42 is provided with a load cell 56. The number of load cycles is counted as the number of oscillations. Equivalently for the present purposes, the apparatus 40 may be provided with a light source 58 that produces a light beam and a photodetector 60 that receives and measures the light beam. The light source 58 and photodetector 60 are positioned so that the shaft blank breaks the light beam as it oscillates, and the number of oscillations is determined from the number of times the light beam is broken.

From the number of oscillations in a period of time, the longitudinal vibrational frequency is determined in a controller 62. Based upon the longitudinal vibrational frequency determined for the golf shaft blank 20 and its relation to the nominal frequency desired, the golf shaft blank 20 is repositioned by moving it parallel to its longitudinal axis 21, numeral 34. If the measured frequency is greater than the desired nominal frequency, the golf shaft blank 20 is moved so as to lengthen the cantilevered length (to the right in the view of FIG. 3). If the measured frequency is less than the desired nominal frequency, the golf shaft blank 20 is moved so as to shorten the cantilevered length ( to the left in the view of FIG. 3). The amount by which the golf shaft blank 20 is to be moved as a function of the required correction in the vibrational frequency is determined experimentally during initial calibration procedures. Typically, that longitudinal movement amount is about ¼ inch per 3 counts per minute of change required in the vibrational frequency.

To accomplish the movement, the butt clamp 42 is released. The collet service rod 50 then engages the blank tip end 24 and moves it in the appropriate direction. To precisely establish the position to which the golf shaft blank 20 is to be moved, a shaft index rod 64 lying along the longitudinal axis 21 contacts the blank butt end 22. The shaft index rod 64 is locked into its position by one of a plurality of position locks 66. In the preferred embodiment, the controller 62 provides a series of divisions of the frequency relative to the desired nominal frequency, in this case 8 such divisions. The measured blank frequency is placed into the appropriate division, which determines the position lock 66 which is to be actuated.

After the golf shaft blank 20 is repositioned, the butt clamp 42 is reengaged to the repositioned golf shaft blank 20. The collet 48 is removed from the blank tip end 54 by capturing it with an electromagnet on the collet service rod 50.

The golf shaft blank 20 is trimmed at each end by a pair of spaced-apart saw blades 68a and 68b, numeral 36, resulting in a golf shaft of the desired length and longitudinal vibrational properties. The distance D by which the two saw blades 68a and 68b are spaced determines the length of the final shaft. This distance D is set prior to the start of the present processing, or it may be controllably established during processing, as by mounting the saw motors on a track with a controllable drive along the track. Equivalently, a single saw could be used and moved between the ends of the shaft blank, but this approach takes longer than the preferred technique using two spaced-apart saws.

A prototype of the apparatus of the invention has been built and operated, and the resulting golf shafts were checked for their lengths and tested for their vibrational frequencies. In one example, a group of 30 golf shaft blanks initially had actual measured lengths of about 41 inches and actual measured vibrational frequencies of from about 238 to about 262 counts per minute. After processing by the present approach, all of the shafts had lengths of about 39 inches and vibrational frequencies of 250±1 percent counts per minute, the desired values.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. An apparatus for trimming a shaft elongated parallel to a longitudinal direction and having a butt end and a tip end, the apparatus comprising:

an actuatable butt clamp sized to clamp the shaft at a location adjacent to the butt end;

means for measuring a longitudinal deformation of the shaft with the butt clamp engaged to the shaft at a first location along the length of the shaft;

means for longitudinally repositioning the shaft responsive to a measured value of the longitudinal deformation determined by the means for measuring to a second location and for reclamping the shaft using the butt clamp at the second location along the length of the shaft; and means for sawing the shaft to a selected length.

2. The apparatus of claim 1, wherein the means for measuring comprises means for measuring a longitudinal vibrational frequency of the shaft.

3. The apparatus of claim 1, wherein the means for measuring comprises means for measuring a longitudinal deflection of the shaft.

4. The apparatus of claim 1, wherein the means for measuring comprises:

a tip weight operable to be installed on the tip end of the shaft;

a tip weight installing/de-installing head;

a retractable tip support operable to position the tip end of the shaft in operable relation to the tip weight installing/de-installing head;

a shaft exciter positionable to controllably deflect the shaft; and an oscillation counter that counts the number of oscillations of the shaft in a preselected period of time.

5. The apparatus of claim 4, wherein the oscillation counter comprises a load cell.

6. The apparatus of claim 4, wherein the oscillation counter comprises a source of a light beam and a photodetector that receives the light beam, the source and photodetector being positioned such that longitudinal oscillation of the shaft breaks the light beam.

7. The apparatus of claim 1, wherein the means for longitudinally repositioning comprises:

a shaft index rod aligned axially with the butt end of the shaft;

a lock engagable to the index rod to hold the index rod in a preselected position relative to the butt end of the shaft; and a longitudinal drive engagable to the shaft to move the butt end of the shaft into contact with the index rod.

8. The apparatus of claim 1, wherein the apparatus further includes a controller that receives the longitudinal deformation from the means for measuring and determines the second location therefrom.

9. The apparatus of claim 1, wherein the means for sawing includes two saw blades spaced apart by a distance equal to a desired final length of the shaft.

10. An apparatus for trimming a golf club shaft elongated parallel to a longitudinal direction and having a butt end and a tip end, the apparatus comprising:

a butt clamp operable to controllably clamp the shaft at a location adjacent to the butt end;

a tip weight operable to be installed on the tip end of the shaft;

a tip weight installing/de-installing head;

a retractable tip support operable to position the tip end of the shaft in operable relation to the tip weight installing/de-installing head;

a shaft exciter positionable to controllably deflect the shaft;

an oscillation counter that counts the number of oscillations of the shaft in a preselected period of time;

a controller operable to
    receive an output count of the oscillation counter, and
    determine a longitudinal trim location from the output count of the oscillation counter;

means for longitudinally repositioning the shaft to the longitudinal trim location and for reclamping the shaft thereat using the butt clamp; and a pair of saws spaced a selected distance apart and operable to saw the shaft at a first saw location adjacent to the butt end and at a second location adjacent to the tip end, with the shaft clamped at the second location.

11. The apparatus of claim 10, wherein the oscillation counter comprises a load cell.

12. The apparatus of claim 10, wherein the oscillation counter comprises a source of a light beam and a photodetector that receives the light beam, the source and photodetector being positioned such that longitudinal vibration of the shaft breaks the light beam.

13. The apparatus of claim 10, wherein the means for longitudinally repositioning comprises:

a shaft index rod aligned axially with the butt end of the shaft;

a lock engagable to the index rod to hold the index rod in a preselected position relative to the butt end of the shaft; and a longitudinal drive engagable to the shaft to move the butt end of the shaft into contact with the index rod.

14. A method for producing golf club shafts having a preselected length and longitudinal deformation properties, comprising the steps of:

providing a shaft blank having a length substantially greater than the preselected length;

clamping the shaft blank at a test butt location;

measuring the longitudinal deformation properties relative to a test butt location on the shaft blank, while the shaft blank is clamped at the test butt location;

repositioning the shaft blank, responsive to the longitudinal deformation properties measured in the step of measuring, so as to establish a selected butt location;

reclamping the shaft blank at the selected butt location; and trimming the shaft blank to the preselected length relative to the selected butt location, while the shaft blank is reclamped at the selected butt location.

15. The method of claim 14, wherein the step of measuring provides a vibrational frequency in counts per minute, and wherein the step of repositioning includes the step of moving the shaft blank about ¼ inch per 3 counts per minute of desired change in vibrational frequency.

* * * * *